United States Patent [19]

Voigt et al.

[11] 4,278,636
[45] Jul. 14, 1981

[54] CALIBRATING DEVICE FOR A BREATH ALCOHOL MEASURING INSTRUMENT

[75] Inventors: Günter Voigt, Bad Schwartau; Rainer Boldt, Lübeck, both of Fed. Rep. of Germany

[73] Assignee: Drägerwerk Aktiengesellschaft, Fed. Rep. of Germany

[21] Appl. No.: 121,697

[22] Filed: Feb. 15, 1980

[30] Foreign Application Priority Data

Mar. 28, 1979 [DE] Fed. Rep. of Germany ....... 2912181

[51] Int. Cl.$^3$ .................. G01N 33/50; G01N 1/22
[52] U.S. Cl. .................................. 422/84; 23/232 E; 23/907; 128/719
[58] Field of Search ............... 422/84, 103; 23/907, 23/232 E; 128/719, 730; 73/421.5 R

[56] References Cited

U.S. PATENT DOCUMENTS

| 3,940,251 | 2/1976 | Jones et al. | 422/84 |
| 3,948,604 | 4/1976 | Hoppesch | 422/84 |
| 4,163,383 | 8/1979 | Vandersyde et al. | 422/84 X |

FOREIGN PATENT DOCUMENTS 2522932 12/1976 Fed. Rep. of Germany ............ 422/84

Primary Examiner—Ronald Serwin
Attorney, Agent, or Firm—McGlew and Tuttle

[57] ABSTRACT

A calibrating device for a breath alcohol measuring instrument which includes a passage for the breathing air which has a sensor and a collector arranged therein with a discharge to atmosphere from the collector comprises a connecting circuit having valve means for selectively connecting the circuit through the passage. The connecting circuit has a member with a chamber therein which has a piston wall member movable in the chamber between two end positions and spring means biasing it toward one end position. A calibrating gas supply and a sensor are selectively connectable to the chamber on one side of the movable piston wall member. Control means are connected to the chamber and the sensor and to the valve means for selectively connecting either the calibrating gas supply or the sensor to the chamber and to the passage for the breathing air in the measuring instrument.

5 Claims, 1 Drawing Figure

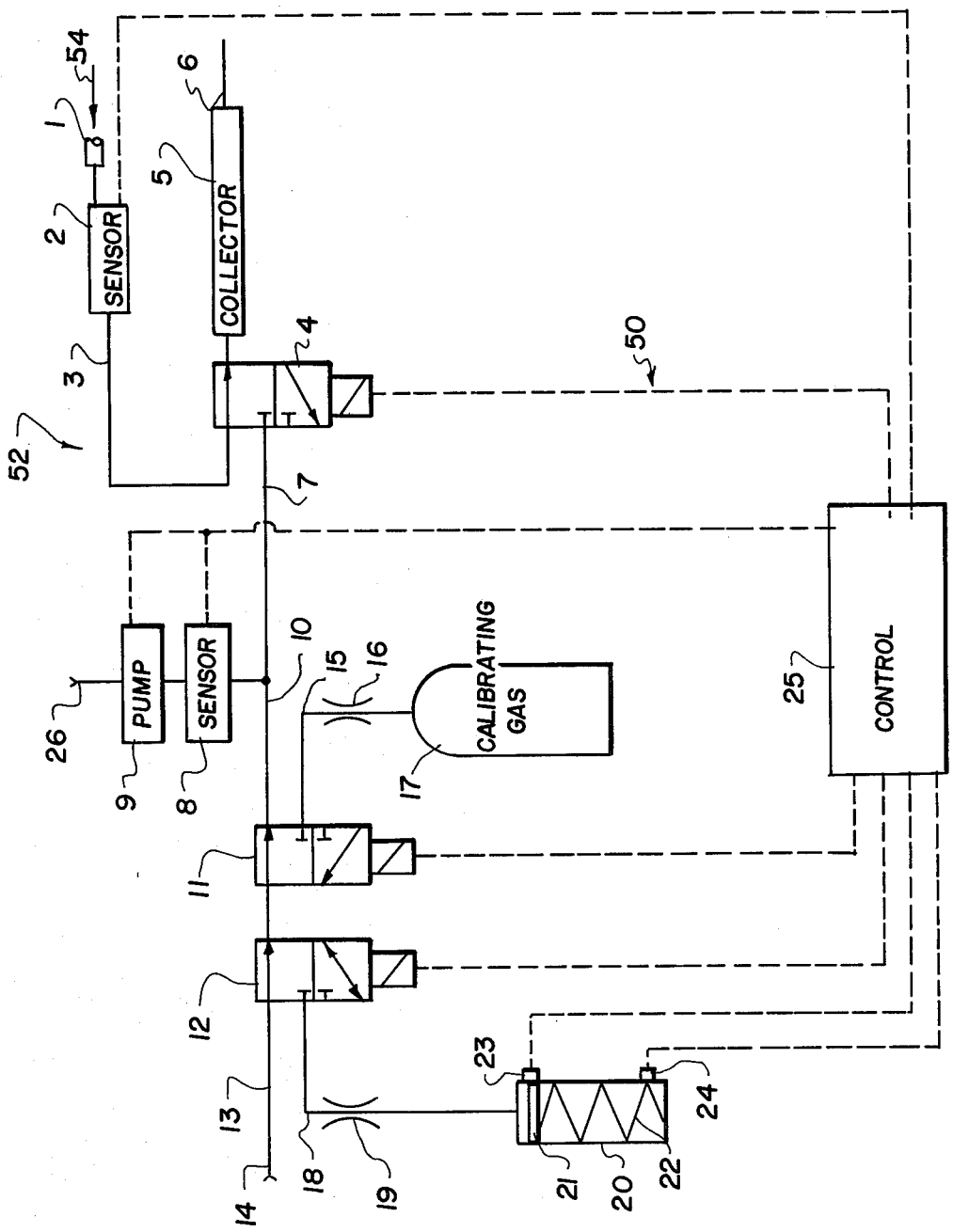

CALIBRATING DEVICE FOR A BREATH ALCOHOL MEASURING INSTRUMENT

FIELD AND BACKGROUND OF THE INVENTION

This invention relates in general to breath alcohol measuring instruments and in particular to a new and useful calibrating device for such instruments.

Measuring instruments with semiconductor sensors in which the electrical conductivity of the sensor material is influenced by the adsorption of gas need a possibility for calibration because the semiconductor sensor signal varies due to use and aging. Depending on performance and accuracy required, calibration may also be necessary in shorter time intervals.

One known calibrating device for equipment for the automatic analysis of traces of organic solvent vapors in air, using a semiconductor sensor, consists of a thermo-insulated and heated tank like a washing bottle filled to a part of its height with liquid solvent. Disposed in the liquid and projecting into the gas-filled space of the tank is an evaporating device comprising a filter paper folded in star form. An inlet tube for the air ends above the liquid level. The outlet for the discharge of the solvent/vapor concentration from the calibrating device is located in an upper dome of the tank. The outlet empties via a capillary and a control valve in the test gas line. The test gas line is connected to the semiconductor sensor, which is followed by a flow regulator and the gas pump. A program switching mechanism takes care of the switching between measuring and calibrating in fixed time intervals. During the measuring phase the air to be tested is sucked by the pump through the test gas line to the semiconductor sensor. During the calibrating phase a filter is inserted upstream of the test gas line to rid the air of the measuring component. Then the underpressure prevailing in the test gas line attracts, through the capillary and the open control valve, solvent vapor from the calibrating device, which mixes with the test gas line air free of the measuring component, and feeds it to the semiconductor sensor. To prevent condensation from the solvent vapor then standing in the outlet upon the conclusion of the calibration, a bypass line, provided with a capillary, connects the outlet constantly to the flow regulator and the pump while bypassing the control valve and the semiconductor sensor. Thus, a part flow is taken from the calibrating device constantly to replenish the content of the outlet. It is disadvantageous that the device is position-dependent due to the use of liquid. The concentration formed in the calibrating device depends greatly on the temperature which must be kept constant by costly insulation and additional heating with high energy requirement. In addition to previous condensations, the concentration contained in the test gas line is also affected by the flow and pressure conditions at the mixing point and impaired in its reliability (DE-PS 24 22 271).

In a known device for the detection and quantitive analysis of a gas, a sample, such as a breath sample to be tested for alcohol, is blown into a sample collector. The sample collector is a wound, narrow tube with a thermal jacket, open to environment at one end, and alternately connected at the other end to the blow-in opening, the electrochemical sensor, or a calibrating device. For measuring, the gas is sucked by a pump from the sample collector through the sensor and a flow meter and measured by the sensor. Each measurement is preceded by a calibration. For this purpose, the sensor is connected first to the blow-in opening, and ambient air is attracted by the pump for flushing. At the same time, the sample collector is connected to the calibrating device, a compressed gas cylinder containing air and ethanol vapor. The composition is selected so that no ethanol condenses at the lowest operating temperature, and that no water vapor is present either. When an actuating button is depressed, calibrating gas flows from the compressed gas cylinder into the sample collector, filling it. This calibration sample is subsequently fed to the sensor and the latter's display corrected according to the known concentration. Disadvantageous is that no means are provided to determine the amount of calibrating gas filled into the sample collector. If the actuating button is pushed too briefly, the amount is too small, and the calibration leads to faulty results. When pushed too long, the sample collector becomes over-filled, and calibrating gas discharges into the atmosphere at its open end and is lost. Thus, the calibrating gas supply is exhausted prematurely (DE-OS 22 40 422).

SUMMARY OF THE INVENTION

The invention provides a calibrating device which assures definite calibration while consuming gas economically and requiring no additional energy.

In accordance with the invention the calibrating device for the breath alcohol measuring instrument includes a calibrating gas which is connectable through various valve systems in a circuit to a chamber in which a wall piston member is movable. In addition, a pump and a sensor is connected to the chamber. The entire circuit is connectable to the instrument which includes a gas sensor as well as a collector in a passage for the breathing air. A control member in the circuit permits selective connection of the calibrating gas in the sensor to the chamber containing the movable wall piston member. The circuit is connectable to the testing instrument breathing gas passage through a valve which is actuated by the control.

According, thereto, the exact amount of calibrating gas required for each calibration is made available by filling the chamber. This precludes faulty measurements. It also prevents losses and achieves a long useful life with a small supply of calibrating gas, which has a beneficial effect on portable instruments. Irrespective of the fluctuating pressure of the calibrating gas supply, in the chamber it is always under the same pressure determined by the spring force and, therefore, is supplied to the semiconductor sensor under defined conditions. Accordingly, defined calibrations are assured.

By providing a compressed gas tank as a calibrating source makes application independent of position possible, due to the gaseous filling with always uniform concentration of the calibrating gas. Heating and the energy sources associated therewith are not needed.

An evaporator may also be used to provide the calibrating gas, the calibrating gas formed being supplied to the semiconductor sensor in defined manner and economically by the chamber.

Programmed calibration cycling is possible and avoids mistakes through errors or unnoticed exhaustion of the calibrating gas supply.

By locating the choke upstream, calibration problems which are due to excessive flow velocities at high calibration gas supply pressure are prevented.

Accordingly, it is an object of the invention to provide a calibrating device for a breath-alcohol measuring instrument including a passage for breathing air which has a sensor and a collector arranged therein and includes a discharge to atmosphere connected to the collector which comprises a connecting circuit and valve means for selectively connecting the circuit to the passage, wherein the circuit includes a member having a chamber therein with a piston wall movable in the chamber between two end positions and biased by spring means into one end position and which further includes a calibrating gas supply connectable to the chamber on one side of the piston as well as a sensor connected to the chamber on one side of the piston, and control means connected to the chamber and to the sensor and to the valve means for selectively connecting the calibrating gas to the chamber and the sensor to the chamber and the circuit to the gas passage.

A further object of the invention is to provide a calibrating device which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWING

In the drawing:

The only FIGURE of the drawing is a schematic diagram of a calibrating device and an alcohol breath detection instrument constructed in accordance with the invention.

DESCRIPTION OF THE PREFERRED EMBODIMENT

Referring to the drawing, in particular the invention embodied therein comprises a calibrating device generally designated 50 which is selectively connectable to an instrument generally designated 52 for analyzing the alcohol content of a breathing gas. The breathing gas is directed in the direction of an arrow 54 through a mouthpiece 1 of a tubular member 3 defining a breathing gas passage having a sensor 2 and a collector 5 therein. The instrument 52 is connectable to the circuit 50 by valve means in the form of a switching valve 4 arranged in the circuit 50.

In accordance with the invention the breath alcohol detecting instrument 52 includes a blow-in opening 1 which is connected via the flow sensor 2, the line 3 and the first valve 4 to a heated sample collector 5 which has a spiral coil open to the environment at its end 6. Through a line 7, a first valve 4 is connected to a heated semiconductor sensor 8 and a pump 9 is following it. Furthermore, the semiconductor sensor 8 is connected, through a line 10, a second valve 11 and a third valve 12, to a line 13 whose end 14 opens into the environment. A calibration gas source 17 is connected to a second valve 11 via a line 15 containing the choke 16. A cylindrical chamber 20 is connected to a third valve 12 via a line 18 containing a choke 19. Movable as a piston in chamber 20 against the force of a spring 22 is the moving wall 21. Limit switches 23 and 24 are connected to the control unit 25, signalling to it the attainment of the empty or full position by the wall 21. Also connected to the control unit 25 are the drives of the valves 4, 11 and 12 as well as the flow sensor 2, semiconductor sensor 8, and pump 9.

Thus, the addition to controlling the discharges, the control unit 25 also carries out storage and display of the value measured.

When activated by the control unit 25, the valves attain the switched position from the basic position shown. In the basic position, the first valve 4 connects the sample collector 5 to line 3 and blocks line 7; in switched position, it connects the sample collector 5 to line 7 and blocks line 3. In its basic position, the second valve 11 connects line 10 to the third valve 12 and blocks line 15; in switched position, it connects line 15 to the third valve 12 and blocks line 10. In its basic position, the third valve 12 connects line 13 to the second valve 11 and blocks line 18; in switched position it connects the second valve in the line 18 and blocks line 13. The pump 9 is running during the entire operating time and attracts through the semiconductor sensor 8 a constant gas flow which discharges into the atmosphere at Due to the uniform flow, the semiconductor sensor 8 can be kept at a uniform operating temperature.

In the basic position, ambient air is attracted at the end 14, reaching the semiconductor sensor 8 through line 13, valves 12 and 11, and line 10. Starting from the basic position, either a calibration can be made or a person tested.

The execution of a calibration test is triggered by depressing a key of the control unit 25. This brings the valves 4,11,12 into their switched positions. Now ambient air is attracted at end 6, reaching the semiconductor sensor 8 through the sample collector 5, the first valve 4 and line 7. At the same time, the calibration gas source 17 is connected to the chamber 20 through the valves 11 and 12. The calibration gas source 17 is a compressed gas tank, approximately 200 cm$^3$ in size, in which the calibrating gas is stored single-phase under the initial overpressure of about 8 bar. It consists of a mixture of air and about 1 $\mu$l alcohol. This mixture is gaseous at ambient temperature, no condensation occurring. The calibration gas reaches the chamber 20 in a flow limited by the chokes 16 and 19 and moves the wall 21 into the full position, countering the force of spring 22. Irrespective of the pressure in the calibration gas source 17, the filled chamber 20, having a capacity of about 2 cm$^3$, contains the calibrating gas always under the same overpressure of about 1.5 bar, brought about by the spring force. The amount of gas thus determined is fixed so that it certainly suffices to carry out the calibration test. When it becomes impossible to fill the chamber 20 because the calibration gas source 17 is empty, and the wall 21 does not reach the empty position, continuation of the cycle is interrupted by the control unit 25. At the conclusion of the filling operation the wall 21 actuates the limit switch 24 and triggers switching of the valves 11 and 4 into their basic positions by the control unit 25, whereas the third valve 12 remains in its switched position. Thus, line 7 is closed by the first valve 4. The calibrating gas contained in chamber 20 flows through the choke 19, the line 18, the valves 12 and 11, and line 10 to the semiconductor sensor 8, and thence pump 9 into the open. The calibration test is carried out by the semiconductor sensor 8 in the process. Since always the same chamber filling flows in at the pressure exerted by spring 22, each calibration test results in a reproducible curve. At the end of the emptying stroke the wall 21 actuates the limit switch 23. The control unit 25 then terminates the calibration test by switching the third valve 12 into its basic position. With this, the entire arrangement is in its basic position again.

Testing a test person starts with blowing exhaled air into the blow-in opening 1, the flow sensor 2 triggering the control unit 25. The exhaled breath flows through the flow sensor 2, line 3 and the first valve 4 into the sample collector 5, filling it and displacing the former content of the sample collector 5 into the environment at the open end 6. The signals of the flow sensor 2 then cause the control unit 25 to bring the valves 4 and 12 into their switched positions. This blocks line 10, as no flow can emanate from the empty chamber 20. The breath sample is pumped from the sample collector 5 through the first valve 4, the line 7 and the semiconductor sensor 8. The maximum of the sensor signal is stored in the control unit 25 and displayed as a measured value. Immediately following the breath sample, ambient air is pumped which is attracted from the end 6 of the sample collector 5. Residues of the breath sample are thus flushed out of the train of lines from the sample collector 5 to the semiconductor sensor 8. As soon as the sensor signal has resumed its basic value for ambient air, the control unit 25 returns the valves 4 and 12, and hence the entire arrangement, into the basic position again.

While specific embodiment of the invention has been shown and described in detail to illustrate the application of the principles of the invention, it will be understood that the invention may be embodied otherwise without departing from such principles.

What is claimed is:

1. A calibrating device for a breath-alcohol measuring instrument which includes a passage for the breathing air having a sensor for detecting alcohol therein and a collector in the passage arranged after the sensor and having an atmospheric discharge, comprising a connecting circuit, valve means in said circuit for selectively connecting the circuit to said passage, said circuit also including a member therein having a chamber, a piston wall movable in said chamber between two end positions, spring means biasing said piston wall member toward one end position, a calibrating gas supply connectable to said chamber on said one end of said piston, a sensor connected to said chamber on one side of said piston, and control means connected to said chamber and to said sensor and said valve means for selectively and alternatively connecting said sensor and said calibrating gas supply to said chamber and for connecting said circuit to said breathing gas passage.

2. A calibrating device according to claim 1, wherein said calibrating gas source comprises a compressed gas tank filled with a calibrating gas.

3. A calibrating device according to claim 1, wherein said calibrating gas source comprises an evaporator connected to a compressed gas supply.

4. A calibrating device according to claim 1, including a limit switch associated with said member on each side of said chamber actuated by said movable wall in each respective end position, a control connected to each of said limit switches and first and second additional valve means in said circuit connectable to said sensor and to said calibrating gas supply.

5. A calibrating device according to claim 4, including a choke connected between said one side of said chamber and said compressed gas supply.

* * * * *